(12) United States Patent
La Vean

(10) Patent No.: US 10,874,432 B2
(45) Date of Patent: Dec. 29, 2020

(54) CONCEPTION DEVICE AND RELATED METHODS

(71) Applicant: Conceivex, Inc., Bloomfield Hills, MI (US)

(72) Inventor: Michael La Vean, Saranac, MI (US)

(73) Assignee: Conceivex, Inc., Bloomfield Hills, MI (US)

( * ) Notice: Subject to any disclaimer, the term of this patent is extended or adjusted under 35 U.S.C. 154(b) by 259 days.

(21) Appl. No.: 15/968,444

(22) Filed: May 1, 2018

(65) Prior Publication Data

US 2019/0336167 A1 Nov. 7, 2019

(51) Int. Cl.
*A61B 17/425* (2006.01)
*A61F 5/455* (2006.01)
*A61F 13/20* (2006.01)

(52) U.S. Cl.
CPC ............ *A61B 17/425* (2013.01); *A61F 5/455* (2013.01); *A61F 5/4553* (2013.01); *A61F 13/2045* (2013.01)

(58) Field of Classification Search
CPC ....... A61F 13/2045; A61F 5/455–4556; A61H 19/00–50; A61H 21/00; A61B 17/425–43
See application file for complete search history.

(56) References Cited

U.S. PATENT DOCUMENTS

| | | | |
|---|---|---|---|
| 2,079,022 A | 5/1937 | Martin | |
| 2,141,040 A | 12/1938 | Holt | |
| 2,324,656 A | 7/1943 | Vincent | |
| 2,423,356 A | 7/1947 | Waterbury | |
| 2,534,900 A | 12/1950 | Chalmers | |
| 2,764,975 A | 10/1956 | Greenberg | |
| 2,818,856 A | 1/1958 | Kohl | |
| 2,836,177 A | 5/1958 | Sells | |
| 2,855,932 A | 10/1958 | Stubbs | |
| 3,037,508 A | 6/1962 | Friedman | |
| 3,371,664 A | 3/1968 | Pleshette | |
| 3,404,682 A | 10/1968 | Waldron | |
| 3,952,737 A | 4/1976 | Lipfert et al. | |
| 4,198,965 A | 4/1980 | Strickman et al. | |
| 4,198,976 A | 4/1980 | Drobish et al. | |

(Continued)

FOREIGN PATENT DOCUMENTS

| | | |
|---|---|---|
| WO | WO 99/36010 | 7/1999 |
| WO | WO 99/37259 | 7/1999 |
| WO | WO 2006/58409 | 6/2006 |

OTHER PUBLICATIONS

International Search Report of corresponding International Application PCT/US19/30169, dated Jul. 10, 2019.

(Continued)

*Primary Examiner* — Thaddeus B Cox
(74) *Attorney, Agent, or Firm* — Fishman Stewart PLLC

(57) ABSTRACT

A conception device includes a dome having a collapsible sidewall, an annular rim, an integral dome rib, and three or more gripping flanges along the inner surface of the rim. The gripping flanges may effectively position and secure the device over the cervix for the concentration of semen on the cervical os to effect fertilization independently or with the aid of biologically active agents. The device may additionally include a handle extending from the annular rim at an angle.

25 Claims, 14 Drawing Sheets

(56) References Cited

U.S. PATENT DOCUMENTS

| | | |
|---|---|---|
| 4,200,090 A | 4/1980 | Drobish |
| 4,200,091 A | 4/1980 | Del Conte |
| 4,219,016 A | 8/1980 | Drobish et al. |
| 4,300,544 A | 11/1981 | Rudel |
| 4,304,226 A | 12/1981 | Drobish et al. |
| 4,311,543 A | 1/1982 | Strickman et al. |
| 4,320,751 A | 3/1982 | Loeb |
| 4,348,321 A | 9/1982 | McDaniel, Jr. et al. |
| 4,360,013 A | 11/1982 | Barrows |
| 4,381,771 A | 5/1983 | Gabbay |
| 4,393,871 A | 7/1983 | Vorhauer et al. |
| 4,401,534 A | 8/1983 | Goepp et al. |
| 4,553,972 A | 11/1985 | Vickery |
| 4,589,880 A | 5/1986 | Dunn et al. |
| 4,630,602 A | 12/1986 | Stickman et al. |
| 4,640,272 A | 2/1987 | Monett |
| 4,703,752 A | 11/1987 | Gabbay |
| 4,770,167 A | 9/1988 | Kaali et al. |
| 4,785,804 A | 11/1988 | Tlapek et al. |
| 4,821,741 A | 4/1989 | Mohajer |
| 4,895,170 A | 1/1990 | Tlapek et al. |
| 4,959,216 A | 9/1990 | Daunter |
| 4,961,436 A | 10/1990 | Koch |
| 5,027,830 A | 7/1991 | Koch |
| 5,044,376 A | 9/1991 | Shields |
| 5,070,889 A | 12/1991 | Leveen et al. |
| 5,207,232 A | 5/1993 | Shihata |
| 5,295,984 A | 3/1994 | Contente et al. |
| 5,824,053 A | 10/1998 | Khosravi et al. |
| 5,857,959 A | 1/1999 | La Vean et al. |
| 6,230,709 B1 | 5/2001 | La Vean |
| 6,796,973 B1 | 9/2004 | Contente et al. |
| 8,454,493 B2 | 6/2013 | La Vean |
| 2013/0267769 A1* | 10/2013 | La Vean ............... A61B 17/425 |
| | | 600/33 |

OTHER PUBLICATIONS

Supplementary Partial European Search Report for Application No. EP 08713141, dated Aug. 23, 2010.
International Search Report and Written Opinion for International Appl. No. PCT/US2008/000505, dated Jun. 20, 2008.

* cited by examiner

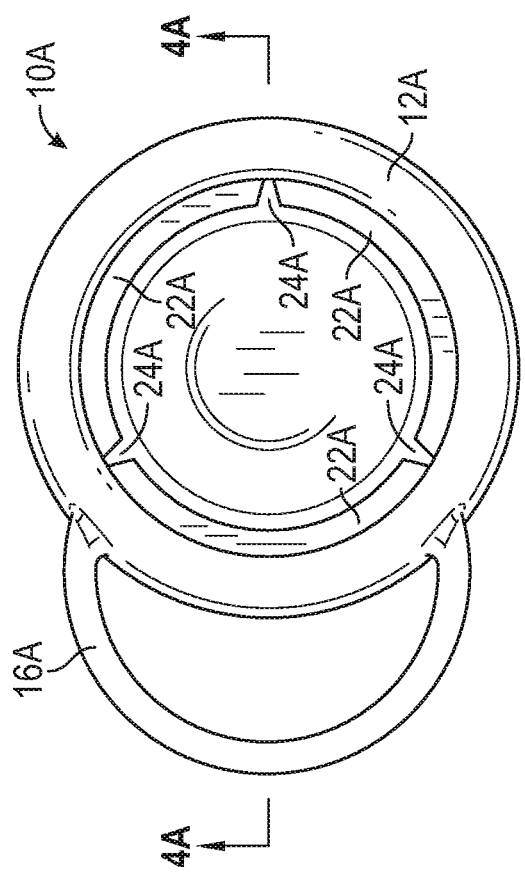
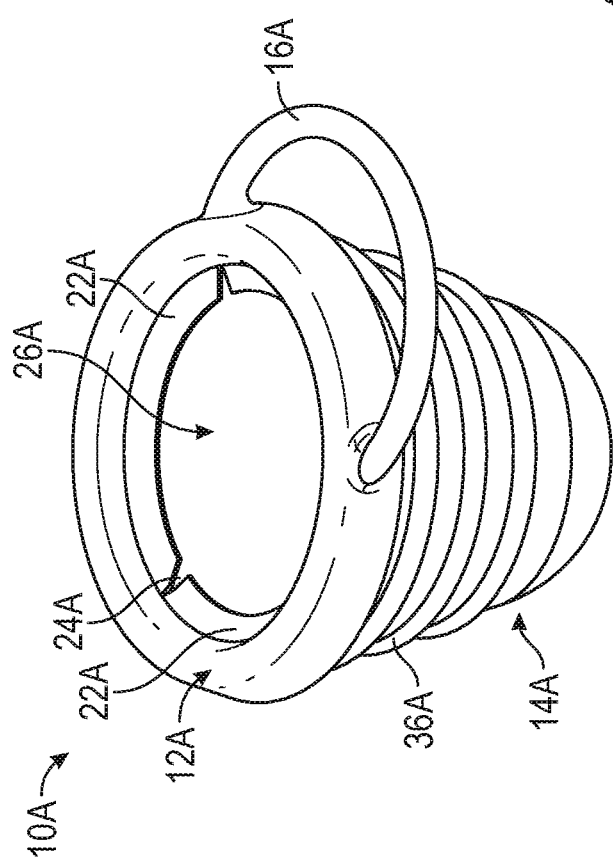
FIG. 2A
FIG. 1A

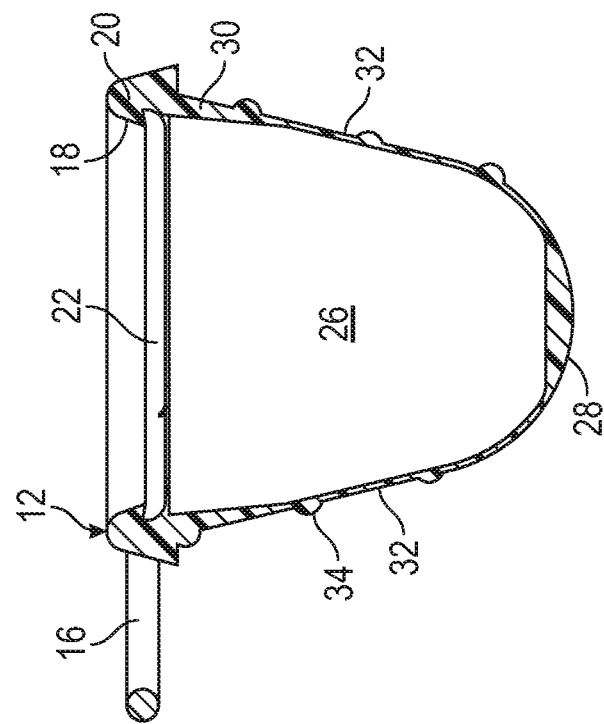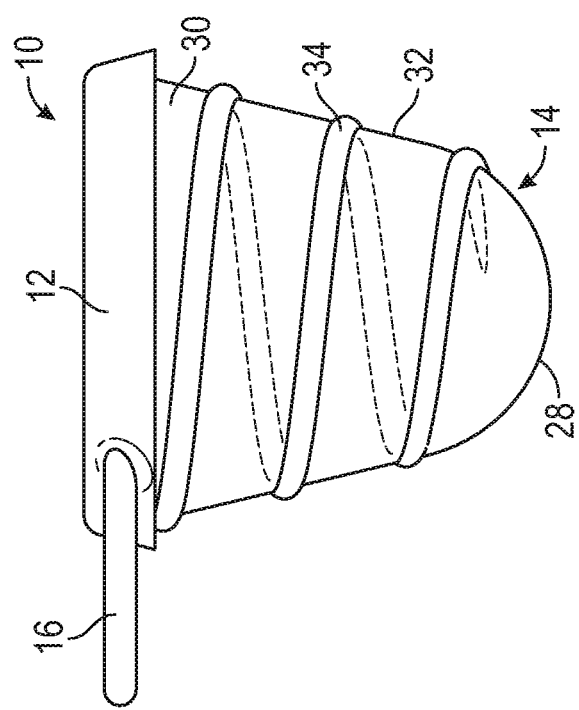

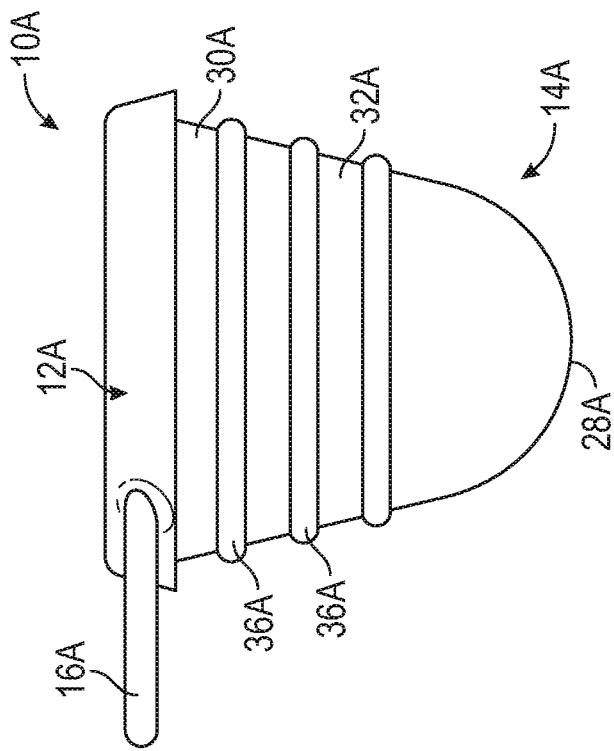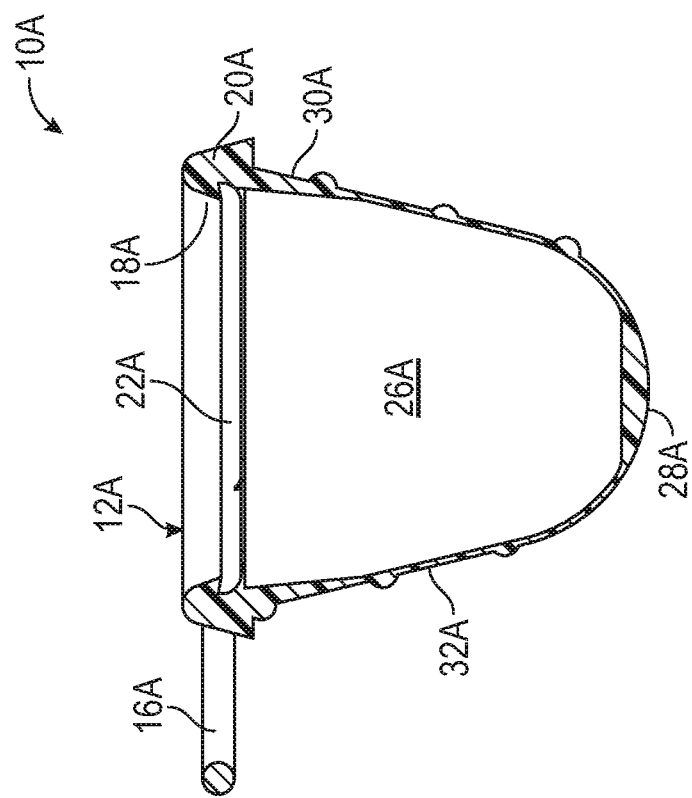

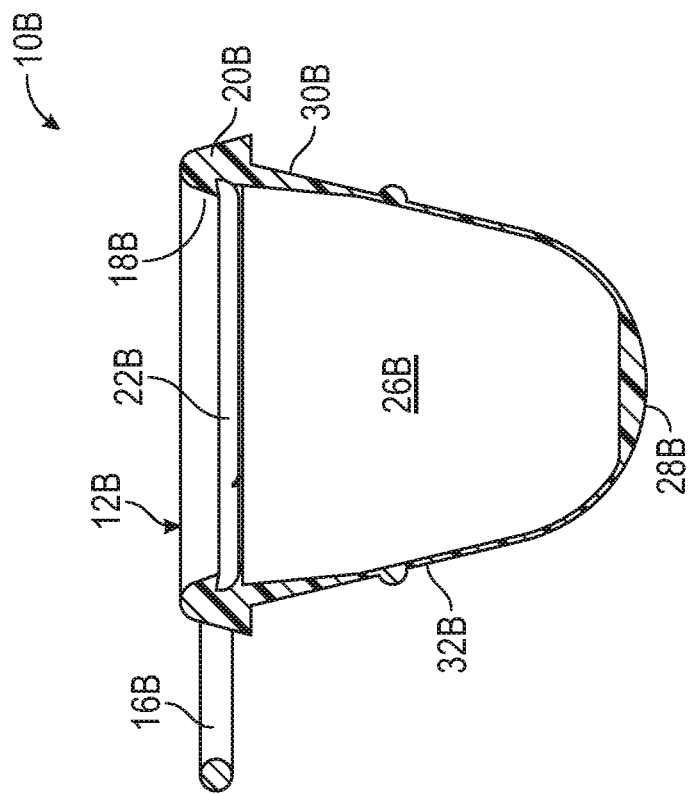
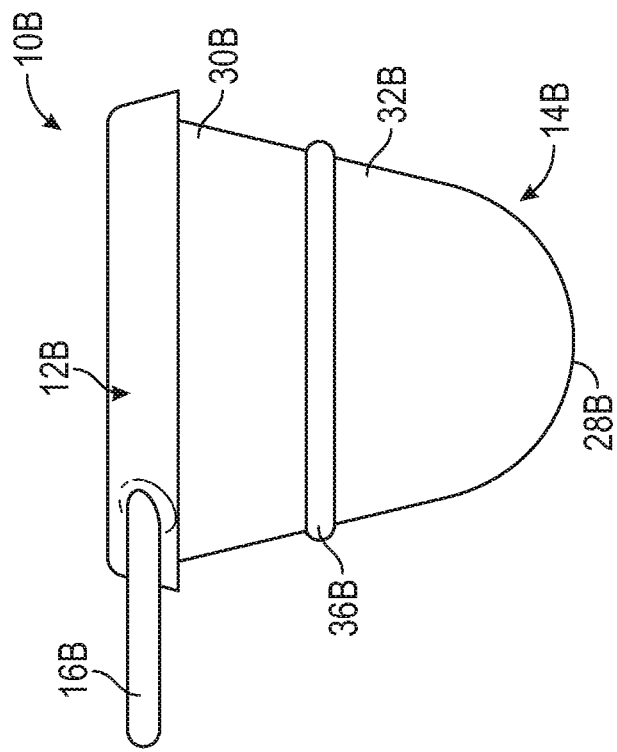

CONCEPTION DEVICE AND RELATED METHODS

FIELD

The present disclosure relates generally to a conception device used to concentrate semen and effect fertilization. The present disclosure also generally relates to a method of conception utilizing the device. Furthermore, the present disclosure relates to a conception device that may be placed by the user in the comfort of her own home and which does not limit normal physical activity while in use.

INTRODUCTION

The statements in this section merely provide introductory information related to the present disclosure and may not constitute prior art.

Medical devices intended to be inserted into the vagina and secured to the cervix are known for use as contraceptive barriers. One particular contraceptive device, the "cervical cap," may be placed over the cervix to prevent semen from entering the cervical canal. The cervical cap may be held in place by a suction grip or surface viscosity on the moist cervical surface. Insofar as known devices are intended for the prevention of pregnancy, latex has proven to be a suitable material. Latex, however, may result in semen damage. Thus, a latex device should not be used for delivery of semen.

To a more limited extent, it is known in the pertinent art to provide a cervical device to position a quantity of semen in proximity to the cervix for purposes of facilitating impregnation. In this regard, U.S. Pat. No. 5,857,959 illustrates and describes a kit for conception developed by the inventors of the present disclosure. The kit generally includes a conception device comprising a thin, form-assuming, flexible dome, an annular rim, and a pair of gripping flanges along an inner surface of the rim for positioning and securing the device over the cervix. The device concentrates semen on the cervical os to effect fertilization. U.S. Pat. No. 5,857,959 is incorporated by reference as if fully set forth herein.

It is also known in the pertinent art to provide a conception device wherein the dome of the conception device is designed to contain semen and, upon securement, properly position a higher concentration of semen in proximity to the cervical os. In this regard, U.S. Pat. No. 8,454,493 illustrates and describes a conception device also developed by the inventor of the present disclosure. That conception device generally includes an annular rim, a dome formed of a unitary construction extending from the annular rim, the dome defining a receptacle area generally including a closed tip, a base portion, and sidewall, and wherein the unitary construction has various thicknesses in a way that the sidewall has the least thickness and is collapsible is a pre-defined manner due to compression by a vaginal cavity which raises the tip toward the annular rim and the cervical os. U.S. Pat. No. 8,454,493 is incorporated by reference as if fully set forth herein. While the kit for conception shown and described in U.S. Pat. Nos. 5,857,959 and 8,454,493 have proven to be extremely successful in promoting pregnancy, continued improvement in the pertinent art remains desirable.

As is generally known, some of the primary factors contributing to a decline in fertility include low semen counts, problems with semen motility, tilted cervix, and a hostile vaginal environment due to infection or other chronic conditions. The present disclosure provides an improved conception device and related method for even more effectively concentrating semen for successful fertilization, thereby even better overcoming the various factors associated with fertility decline, including, but not limited to, the aforementioned factors. The present disclosure also seeks to solve some of the problems associated with the prior art, specifically bunching of the dome of the conception device on the side of the cervix when the vagina goes from actual to potential space, the inability to provide consistent results for women with short cervixes and/or smaller diameter cervixes, and the inability to freeze and transport semen within the conception device. The conception device of the present disclosure may be made of an implantable material such as a silicone-based material, and may be positioned and secured over the cervix while containing semen to facilitate conception. Moreover, the construction of the conception device allows a woman to increase the likelihood of conception within the comfort, convenience and privacy of her own home, and does not limit normal physical activity.

SUMMARY

The present disclosure generally relates to a conception device that is positioned over the cervix to increase the chances of successful fertilization. A dome of the conception device is designed to contain semen and, upon securement, properly position a higher concentration of semen in proximity to the cervical os. The conception device is easily positioned, comfortable to use, and easily removed.

According to one particular aspect, the present teachings provide a conception device that may be positioned over a cervix to concentrate semen and promote fertilization. The conception device may include an annular rim and a dome formed of a unitary construction. The dome may extend from the annular rim and define a receptacle area. The dome may have a closed tip, a base portion, a sidewall extending between the closed tip and the base portion, and an integral dome rib. The sidewall may be collapsible in a predetermined manner. The integral dome rib may be in forms such as a spiral rib or ring ribs on the sidewall. The dome may also be formed to include one or more ridges on the sidewall which connect to the annular rim. The annular rim and the dome are formed of a material suitable for use in the vagina.

According to another particular aspect, the present teachings similarly provide a conception device for positioning over a cervix to concentrate semen and promote fertilization. The conception device may include an annular rim and a dome formed of a unitary construction. The dome may extend from the annular rim and define a receptacle area. The dome may have a closed tip, a base portion, a sidewall extending between the closed tip and the base portion, and an integral dome rib. The conception device may further include at least three thin, gripping flanges projecting radially inwardly from the annular rim. Adjacent flanges may be spaced apart by a notch to permit the flanges to deflect towards the closed tip of the dome during insertion of the device, and to effectively grip and hold the device over the cervix. The dome and the annular rim may be formed of a material suitable for use in the vagina. The integral dome rib may be in forms such as a spiral rib or ring ribs on the sidewall.

According to yet another particular aspect, the present teachings again provide a conception device for positioning over a cervix to concentrate semen and promote fertilization. The conception device may include an annular rim, a dome formed of a unitary construction, and a handle. The annular rim may generally define a plane. The dome may extend from the annular rim and define a receptacle area. The dome may include a closed tip, a base portion, and a sidewall extending between the closed tip and the base portion. The handle may extend from the annular rim at an angle to the plane defined by the annular rim. The dome, annular rim, and handle may be formed of a material suitable for use in the vagina.

According to still yet another particular aspect, the present teachings provide a conception device that may be positioned over a cervix to concentrate semen and promote fertilization. The conception device may include an annular rim and a dome formed of a unitary construction. The dome may extend from the annular rim and define a receptacle area. The dome may have a closed tip, a base portion, a sidewall extending between the closed tip and the base portion, and an integral dome rib. The sidewall may be collapsible in a predetermined manner. The incorporate integral dome rib can have the form of a spiral rib or ring ribs on the sidewall. The dome may also be formed to include one or more ridges on the sidewall which connect to the annular rim. The annular rim and the dome are formed of a material suitable for use in the vagina.

Further areas of applicability of the present teachings will become apparent from the description and appended claims provided hereinafter. It should be understood that the detailed description and specific examples, while indicating the various examples of the present teachings, are intended for purposes of illustration only and are not intended to limit the scope of the teachings.

DRAWINGS

The present teachings will become more fully understood from the detailed description, the appended claims and the following drawings.

FIGS. 1-4 are different views of a conception device in accordance with the present teachings.

FIG. 1 is a perspective view of a conception device in accordance with the present teachings.

FIG. 2 is a top view of the conception device of FIG. 1 in accordance with present teachings.

FIG. 3 is a side view of the conception device of FIG. 1 in accordance with the present teachings.

FIG. 4 is a cross-sectional view taken along line 4-4 of FIG. 2.

FIGS. 1A-4A are different views of another embodiment of a conception device in accordance with the present teachings.

FIG. 1A is a perspective view of another embodiment of a conception device in accordance with the present teachings.

FIG. 2A is a top view of the conception device of FIG. 1A in accordance with present teachings.

FIG. 3A is a side view of the conception device of FIG. 1A in accordance with the present teachings.

FIG. 4A is a cross-sectional view taken along line 4-4 of FIG. 2A.

FIGS. 1B-4B are different views of another embodiment of a conception device in accordance with the present teachings.

FIG. 1B is a perspective view of another embodiment of a conception device in accordance with the present teachings.

FIG. 3B is a side view of the conception device of FIG. 1B in accordance with the present teachings.

FIG. 4B is a cross-sectional view taken along line 4-4 of FIG. 2B.

FIG. 1C is a perspective view of another embodiment of a conception device in accordance with the present teachings.

FIG. 3C is a side view of the conception device of FIG. 1C in accordance with the present teachings.

FIG. 1D is a perspective view of another embodiment of a conception device in accordance with the present teachings.

FIG. 3D is a side view of the conception device of FIG. 1D in accordance with the present teachings.

Figure 2:
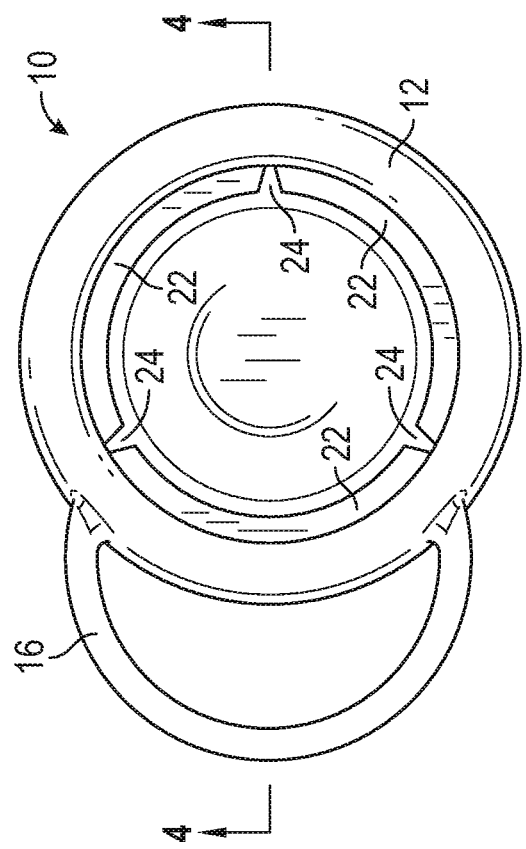

It will be understood that the drawings are not drawn to scale.

DESCRIPTION OF VARIOUS ASPECTS

The following description is merely exemplary in nature and is not intended to limit the present disclosure. It will be understood that corresponding reference numerals indicate like or corresponding parts and features throughout the drawings. The description and any specific examples, while indicating embodiments of the present disclosure, are intended for purposes of illustration only and are not intended to limit the scope of the present disclosure. Moreover, recitation of embodiments having stated features is not intended to exclude other embodiments having additional features, or other embodiments incorporating different combinations of the stated features.

Referring generally to FIGS. 1-4, 1A-4A, 1B-4B, 1C, 3C, 1D, and 3D of the drawings, a conception device in accordance with the present teachings is illustrated and generally identified by numeral 10. The conception device 10 may be utilized in connection with a kit for conception for purposes of promoting pregnancy. Two suitable kits for conception are shown and described in U.S. Pat. Nos. 5,857,959 and 8,454,493 which have been incorporated by reference above. It will be understood, however, that the various teachings of the present disclosure may be employed with other kits for conception within the scope of the present invention.

As shown in FIGS. 2 and 4, the conception device 10 may generally include an annular rim 12, a dome 14, and a handle 16. The annular rim 12 has an inner surface 18 and an outer surface 20. One or more cervical engagement members 22 may radially extend inward from the inner surface 18 of the annular rim 12. The one or more engagement members 22 may include a plurality of flanges 22. The plurality may include two or more flanges 22 extending through approximately 120 degrees or less. As illustrated in FIG. 2, the plurality may include three flanges. In other applications, the plurality may include four or more flanges 22. The flanges 22 may be thin in an axial direction and internally formed with the annular rim 12. Adjacent flanges 22 may be spaced apart by a notch 24.

The flanges 22 and cooperating notches 24 may effectively grip and hold the conception device 10 over the cervix in order to concentrate the semen at the os of the cervix and to successfully effect fertilization. The flanges 22 and notch 24 essentially provide the effect of a Chinese finger puzzle by gripping the side walls of the cervix and holding the conception device 10 when the circumference of the annular rim 12 is fitted around the cervix and slightly expands. The conception device 10 is fixed in place by the use of the flanges 22, rather than merely by suction or surface viscosity.

Because the individual flanges 22 extend through approximately 120 degrees or less, bunching up of the deflected flanges 22 is avoided. Preferably the flanges radially extend inward from the inner surface of the annular rim approximately a half millimeter. These flanges 22 resultantly alleviate abrasions to the cervix. This condition is particularly undesirable in patients with severe tilting of the cervix.

A common conception device 10 may be provided of a size suitable to fit a majority of women. In one application, a common conception device 10 may have an inner diameter of approximately 33 mm. Such an inner diameter may be suitable for parous and nuliparous women.

Figure 1:
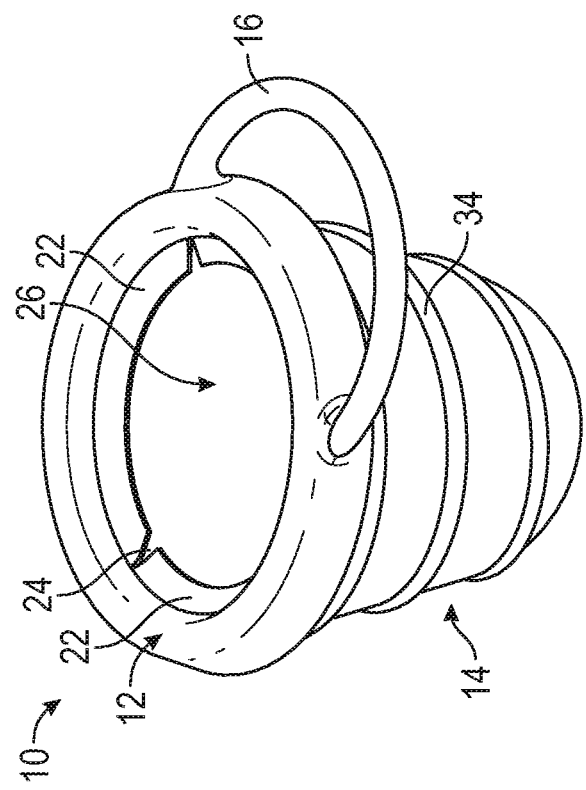
Figure 2B:
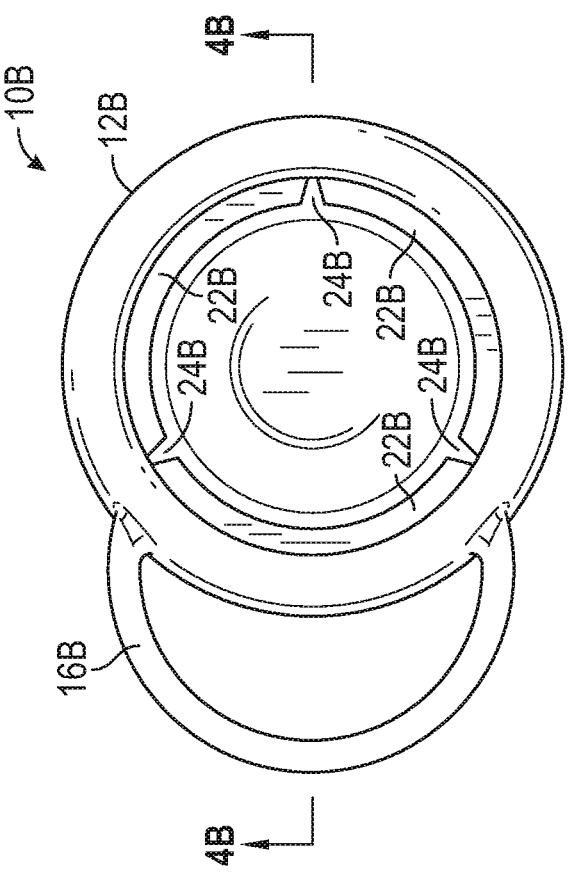
FIG. 2B is a top view of the conception device of FIG. 1B in accordance with present teachings.
Figure 1B:
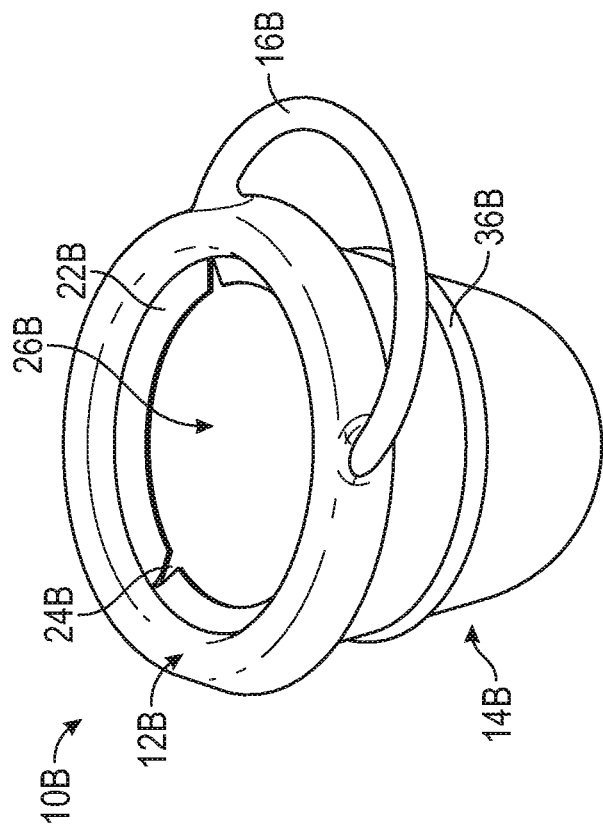

As shown in FIG. 1, the dome 14 may extend from the annular rim 12 and define a receptacle area 26. As shown in FIG. 3, the dome 14 may generally be in the shape of a thimble, and may include a closed tip 28, a base portion 30, and a sidewall 32 extending between the base portion 30 and the tip 28. As will be more appreciated below, the sidewall 32 may be collapsible for proper positioning relative to the cervical os. Such collapse of the sidewall may be particularly useful for treating women with a tilted cervix.

Figure 5A:
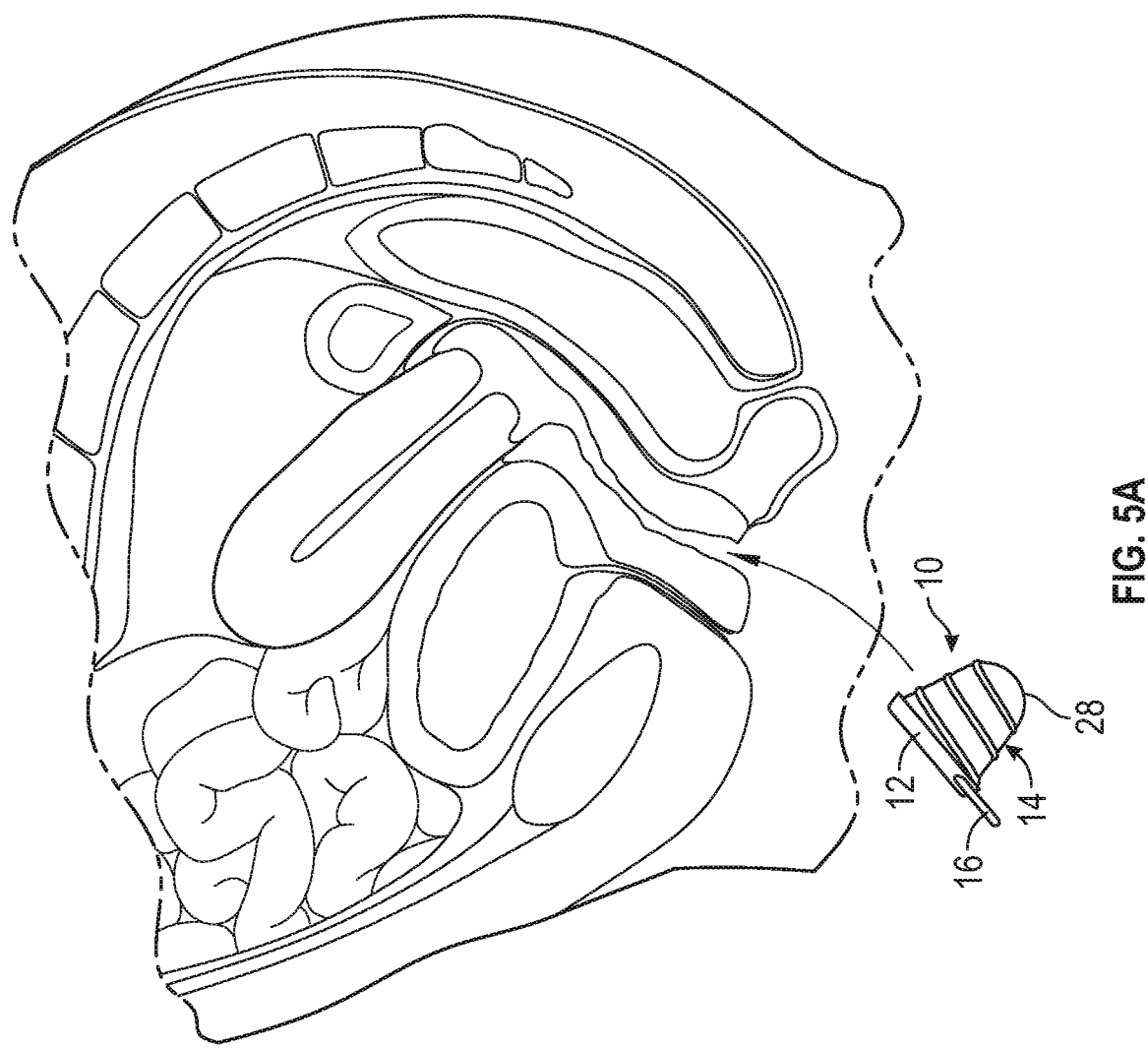
FIG. 5A is a view of a conception device similar to FIG. 1 in use according to the present teachings, illustrating the insertion of the conception device during placement of the conception device.
Figure 5B:
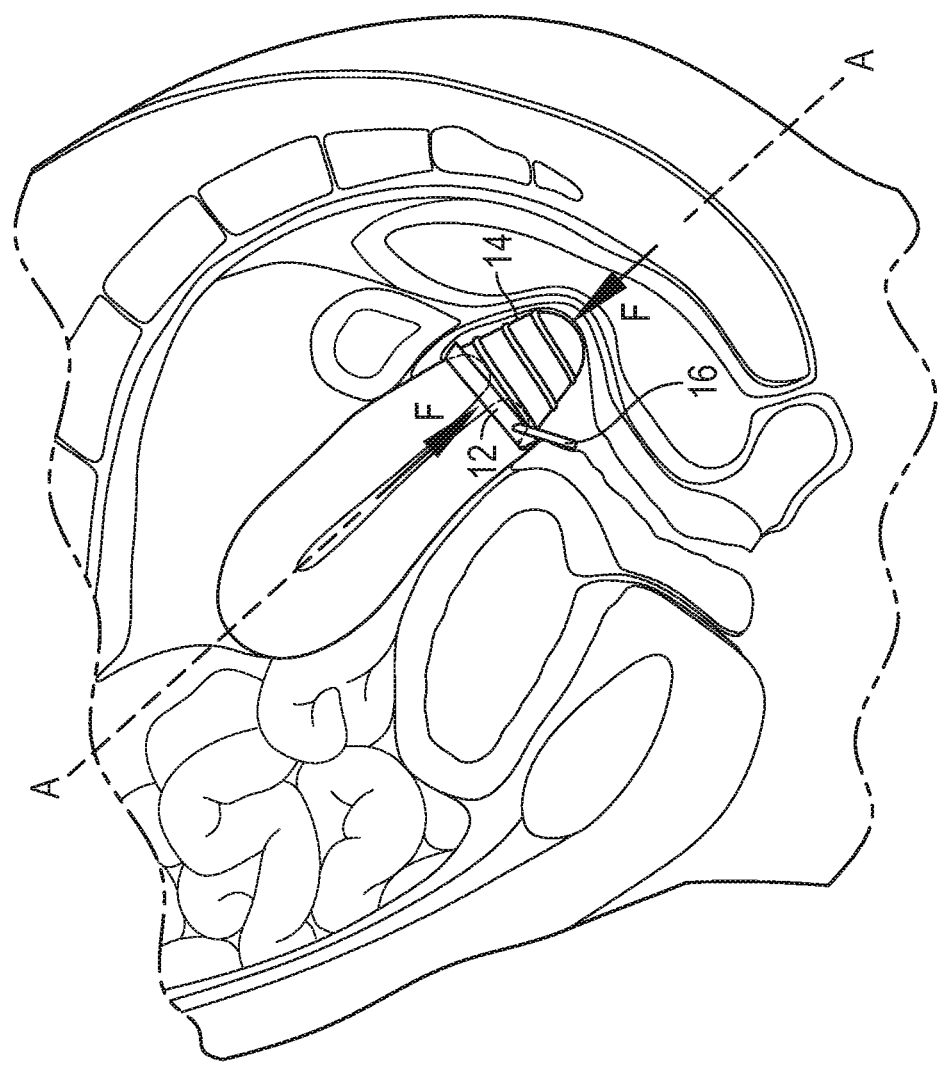
FIG. 5B is a view of a conception device similar to FIG. 1 in use according to the present teachings, illustrating the placement of the dome of the conception device.
Figure 5C:
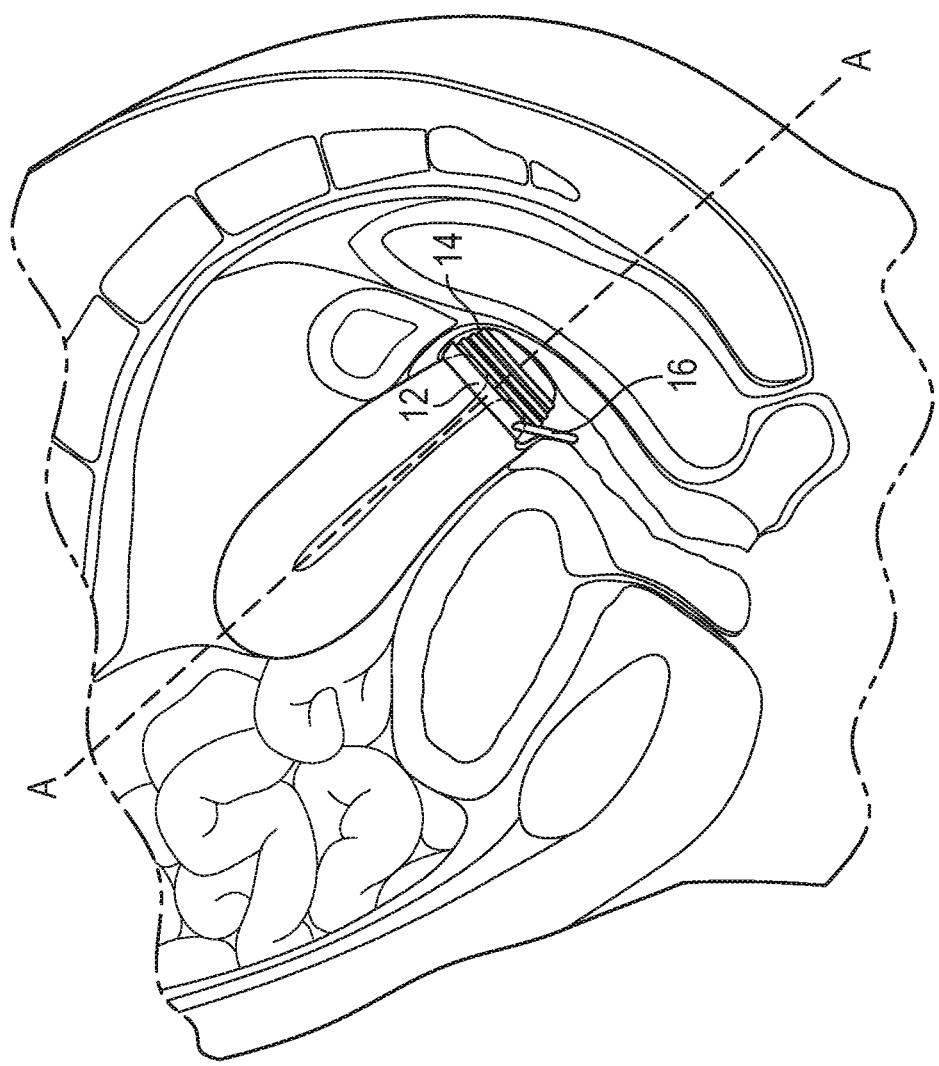
FIG. 5C is a view of a conception device similar to FIG. 1 in use according to the present teachings, illustrating the dome of the conception device as it may collapse during use.
Figure 5D:
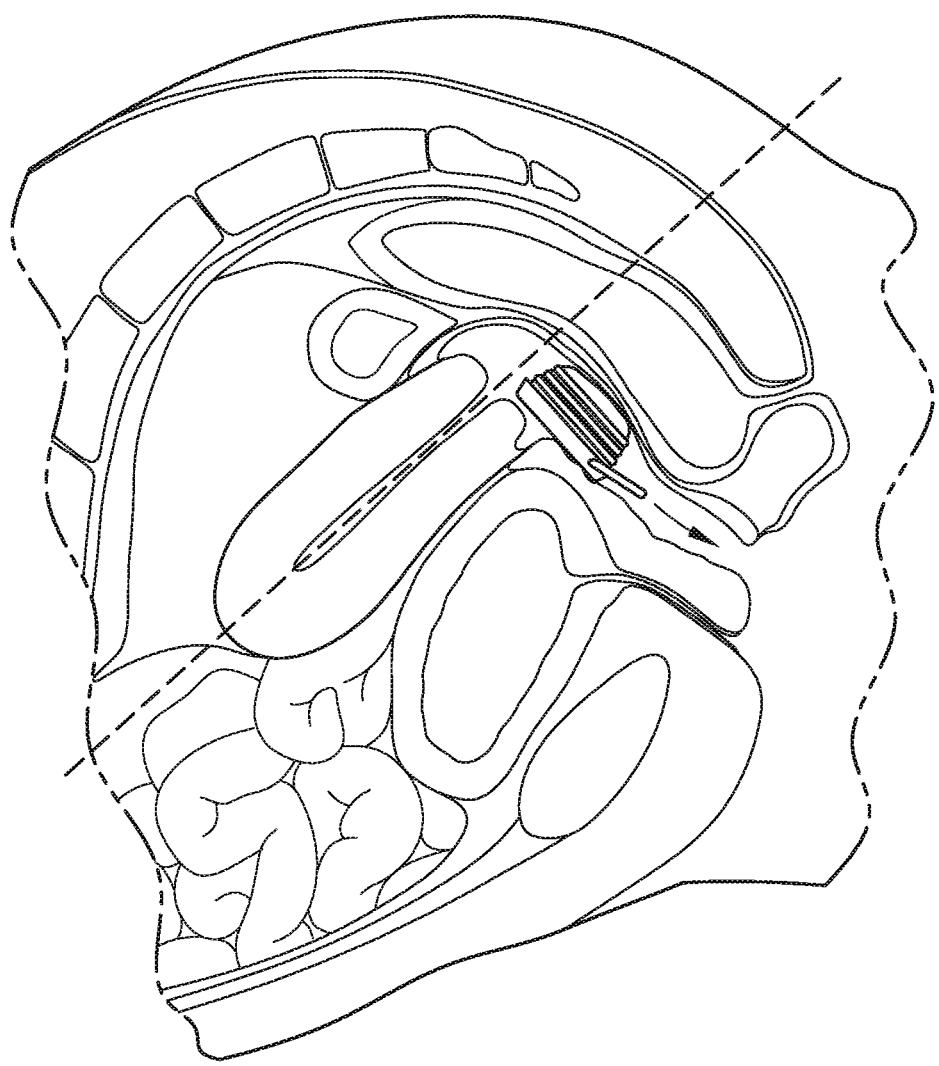
FIG. 5D is a view of a conception device similar to FIG. 1 in use according to the present teachings, illustrating the removal of the conception device.
Figure 7:
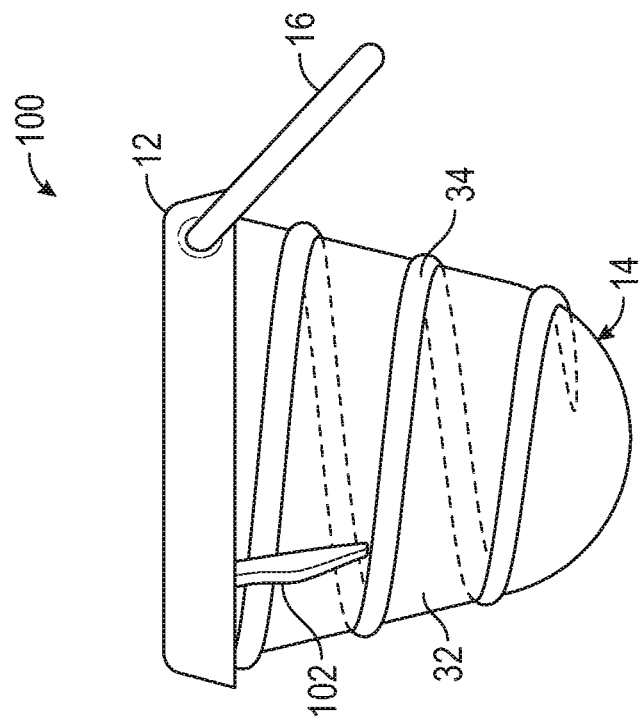
FIG. 7 is a side view of the conception device of FIG. 6.
Figure 6:
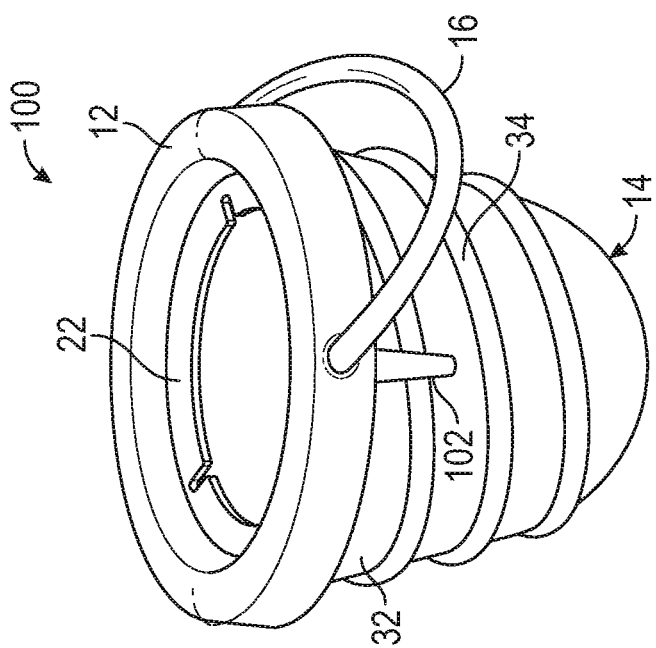
FIG. 6 is a perspective view of yet another embodiment of a conception device in accordance with the present teachings.

The dome 14 may be constructed of a thin, flexible material. Particular materials are addressed below. The dome 14 may be configured to facilitate a desired collapse or predetermined collapse of sidewall 32 which effectively creates a raised floor or tip of the conception device 10. One such configuration is shown in FIG. 5C. In this manner, the contents of the receptacle area 26 is most effectively positioned relative to the cervical os, rather than a pinching of the tip that may undesirably preclude access to the cervical os.

Figure 3C:
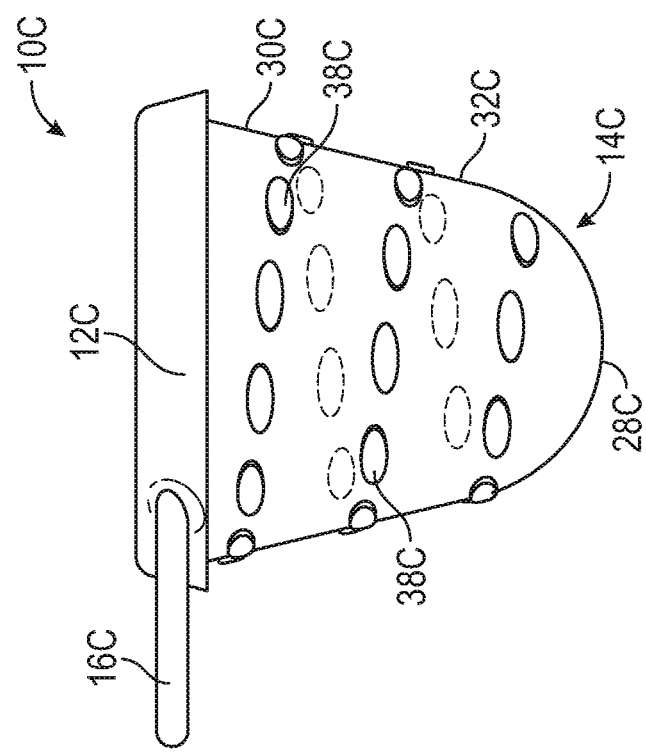
FIGS. 1C and 3C are different views of another embodiment of a conception device in accordance with the present teachings.
Figure 1C:
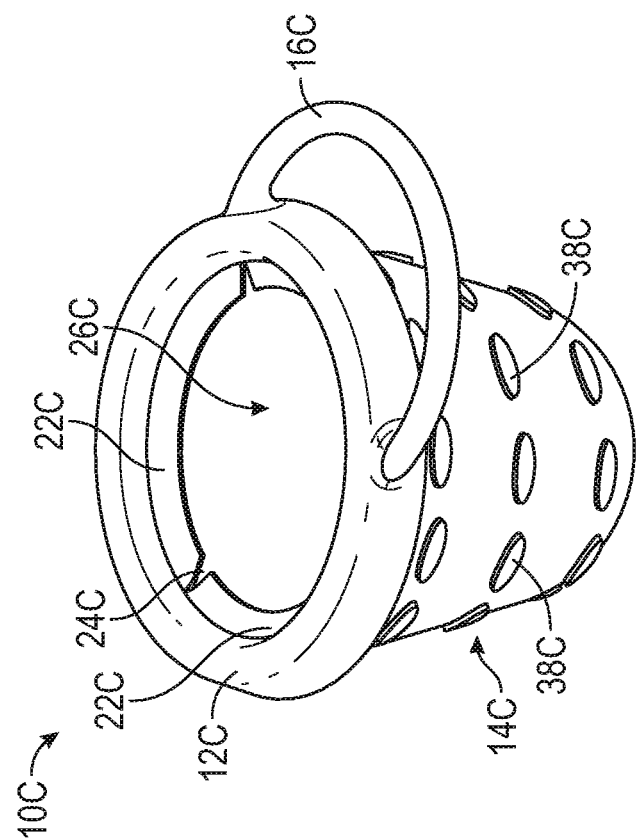
Figure 3D:
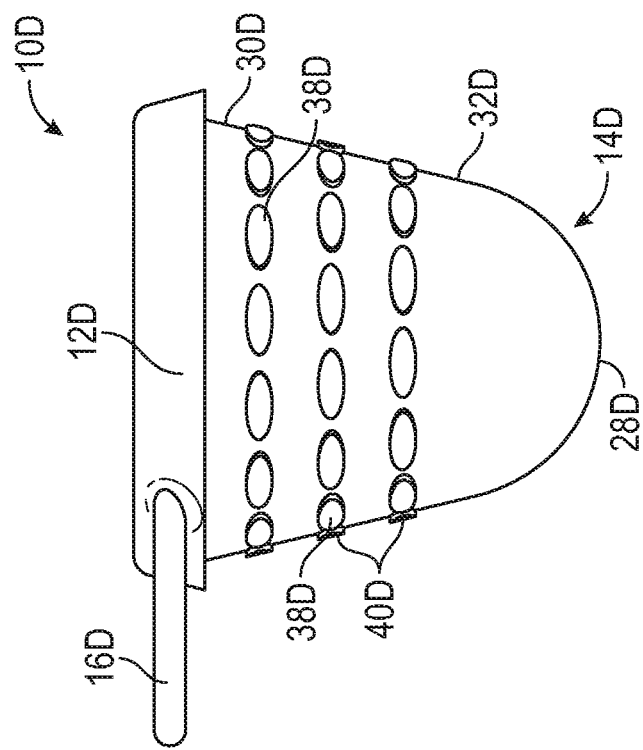
FIGS. 1D and 3D are different views of another embodiment of a conception device in accordance with the present teachings.
Figure 1D:
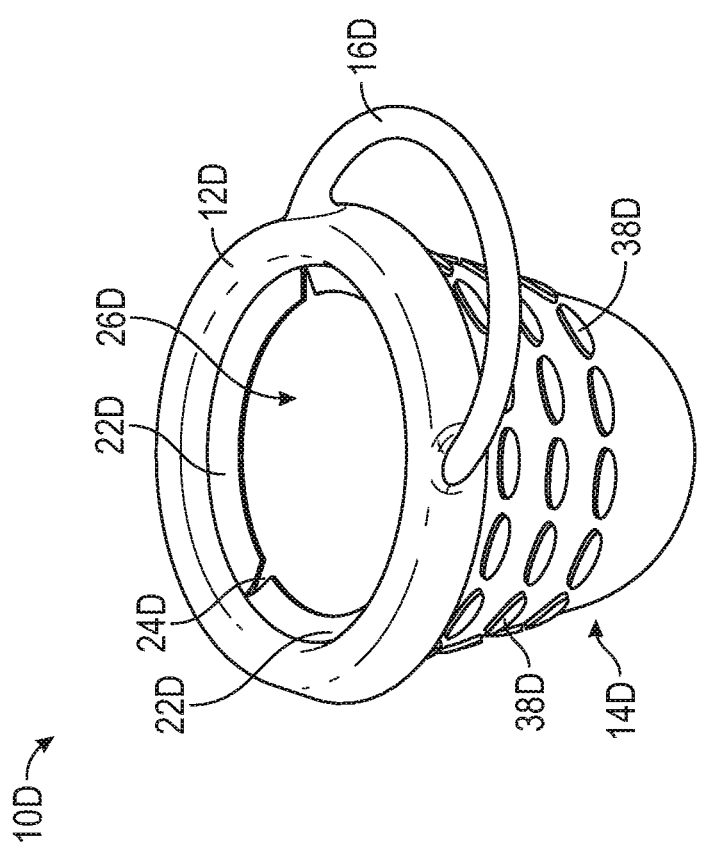

The dome 14 may be formed to incorporate an integral dome rib. The integral dome rib may be a spiral rib 34, as shown in as shown in FIGS. 1-4; one or more ring ribs 36, as shown in FIGS. 1A-4A and FIGS. 1B-4B; a plurality of discrete raised projections 38 placed in a substantially spiral direction pattern, as shown in FIGS. 1C and 3C; or a plurality of discrete raised projections 38 placed in a substantially ring-shaped direction pattern, as shown in FIGS. 1D and 3D.

For example, as shown in FIGS. 1-4, the dome 14 may be formed to incorporate an integral dome rib in the form of a spiral rib 34 along and around the dome 14 extending from the base portion 30 in a continuous downward spiral to the lower portion of the sidewall 32 proximate to the tip 28. The spiral rib 34 is formed as part of the same unitary construction as the dome 14.

The spiral rib 34 effectuates strength, rigidity and lateral stability to the dome 14. The enhanced stability or strength allows the dome to also be constructed of a thicker, flexible material to enable the conception device 10 to be frozen with the sperm inside the receptacle area 26. The spiral rib 34 provides rigidity to cause the predetermined collapse of the sidewall 32. The spiral rib 34 also provides lateral stability which decreases lateral movement of the conception device 10 when in use. In particular, the spiral rib 34 prevents bunching up of the conception device 10 against the side of the cervix when the vagina modifies from actual to potential space. The spiral rib 34 also eliminates an artificial semen pool on the side of the cervix. The spiral rib 34 particularly provides lateral stability to women with a short cervix and/or a smaller diameter cervix, who have less of a natural protrusion to provide the lateral stability on the cervix on its own.

As another example, in alternative embodiments shown in FIGS. 1A-4A and FIGS. 1B-4B, and using FIGS. 1A-4A as the example, the dome 14A may be formed to incorporate an integral dome rib in the form of one or more ring ribs 36A on the sidewall 32A. FIGS. 1A-4A reflects a dome 14A with more than one ring ribs 36A, while FIGS. 1B-4B reflects a dome 14B with one ring ribs 36B. As shown in FIGS. 1B-4B, the ring ribs 36B may extend around the sidewall 32B, around the base portion 30B, or around the sidewall 32B and the base portion 30B. The ring ribs 36B are formed as part of the same unitary construction as the dome 14B. Using FIGS. 1A-4A as the reference, the ring ribs 36A need not be positioned equidistant from each other around the sidewall 32A, around the base portion 30A, or around the sidewall 32A and the base portion 30A so long as the device 10A collapses in the manner desired. However, it is preferable that the ring ribs 36A are positioned equidistant from each other. For any dome 14A having more than one ring rib 36A, the ring ribs 36A are preferably parallel to each other.

Similar to the spiral rib 34 of FIGS. 1-4, the ring ribs 36A and 36B of FIGS. 1A-4A and 1B-4B effectuate strength, rigidity and lateral stability to the dome 14A and 14B, and may be used to allow the conception device 10A and 10B to be frozen with the sperm inside the receptacle area 26A and 26B, to allow for a predetermined collapse of the sidewall 32A and 32B, to prevent bunching of the conception device 10A and 10B, and to provide lateral stability for short or small cervixes.

As yet another example, as shown in FIGS. 1C and 3C, in an alternative embodiment, the dome 14C may be formed to incorporate an integral dome rib in the form of a plurality of discrete raised projections 38C in a substantially spiral direction pattern along and around the outer face of the dome 14C extending from the base portion 30C in a continuous downward spiral to the lower portion of the sidewall 32C. The raised projections 38C are formed as part of the same unitary construction as the dome 14C. The raised projections 38C may take various shapes and sizes as long as the shape and size allow spiraling along the dome 14C. Similar to the spiral rib 34, of FIGS. 1-4, the raised projections 38C effectuate strength, rigidity and lateral stability to the dome 14C, and may be used to allow the conception device 10C to be frozen with the sperm inside the receptacle area 26C, to allow for a predetermined collapse of the sidewall 32C, to prevent bunching of the conception device 10C, and to provide lateral stability for short or small cervixes.

As yet another example, as shown in FIGS. 1D and 3D, in an alternative embodiment, the dome 14D may be formed to incorporate an integral dome rib in the form of a plurality of discrete raised projections 38D in a substantially ring-shaped direction pattern around the dome 14D. As shown in FIG. 3D, the plurality of raised projections 38D may extend in a substantially ring-shaped direction around the sidewall 32D, around the base portion 30D, or around the sidewall 32D and the base portion 30D to form one or more rings 40D around the dome 14D. The plurality of raised projections 38D are formed as part of the same unitary construction as the dome 14D. The rings 40D created by each discrete line of raised projections 38D need not be positioned equidistant around the sidewall 32D, around the base portion 30D, or around the sidewall 32D and the base portion 30D so long as the device 10D collapses in the manner desired. For any dome 14D having more than one ring 40D created by the raised projections 38D, the rings 40D are preferably substantially parallel to each other. The raised projections 38D may take various shapes and sizes as long as the shape and size allow one or more rings 40D along the dome 14D. Similar to the spiral rib 34 of FIGS. 1-4, the incorporation of the plurality of raised projections 38D along the outer wall of the dome 14D effectuates strength, rigidity and lateral stability to the dome 14D, and may be used to allow the conception device 10D to be frozen with the sperm inside the receptacle area 26D, to allow for a predetermined collapse of the sidewall 32D, to prevent bunching of the conception device 10D, and to provide lateral stability for short or small cervixes.

As shown as an example in FIG. 1, the closed tip 28 may include a first thickness and the sidewall 32 may include a second thickness. The first thickness may be greater than the second thickness. In one particular application, the closed tip 28 may have a nominal thickness of approximately 0.035 inches. In this particularly application, a portion of the sidewall 32 may have a nominal thickness of about 0.012 inches. This portion of the sidewall 32 may extend from proximate the closed tip 32 to proximate the base portion 30. A transition area may be defined approximately one-third the way from the annular rim 12 to the closed tip 28 that effectively defines the base portion 30 and has a third thickness. The third thickness may be greater than the second thickness and transition from a thickness of about 0.012 inches to about 0.039 inches.

While the particular dimensions disclosed above have proven suitable for departing a desired collapse of the sidewall 32 during use, other dimensions may be employed within the scope of the present teachings. Particular dimensions will depend on material choices, among other factors. Important to this particular aspect of the present teachings, however, is that the thickness of the closed tip 28 be greater than the thickness of the sidewall 32.

As shown as an example in FIG. 1, the handle 16 may facilitate insertion and removal of the conception device 10 and may be integrally-molded with the annular rim 12. The handle 16 may define a closed loop. The handle 16 may extend from the annular rim 12 at an angle to a plane defined by the annular rim 12. In one application, the handle 16 may extend from the annular arm 12 at an angle of approximately 45 degrees. It will be appreciated that the handle 16 may be oriented relative to the annular rim 12 at other angles within the scope of the present teachings. Preferably insofar as this particular aspect is concerned, the handle 16 is oriented at an angle of at least about 10 degrees and no greater than about 60 degrees.

It is contemplated that dome 14, annular rim 12, gripping flanges 22, and handle 16 will be made of a material suitable to use in the vagina. As used herein, the phase "formed of a material suitable for use in the vagina" shall mean formed of a food grade or better material (e.g., food grade, medical grade, implantable grade, etc.). The device 10 may be formed of a non-resilient flexible material, such as a silicone-based material. This material may or may not be formulated with biologically active components. These components may be released therefrom in an amount effective to achieve its purpose during use.

Types of silicone-based materials suitable for use herein are known in the art and include high-consistency and low-consistency silicone-based elastomers prepared using a variety of well-known methods (e.g., platinum-cured systems) selected for compatibility with biological tissue and particular active ingredients being released by the conception device. An example of a biologically active agent that could be released by the device is one that would alter pH, or effect semen activity.

The conception device 10 may be incorporated into a kit such as that generally described in U.S. Pat. Nos. 5,857,959 and 8,454,493. In addition to the various components described in U.S. Pat. Nos. 5,857,959 and 8,454,493 the kit may include a lubricant and one or more practice devices. The lubricant may be a sperm-friendly intimate moisturizer used to coat the interior of the vagina and the cervix. The practice devices may be shaped like the actual device 10 and allow the user to be comfortable using the device 10.

As shown in FIGS. 5A-5D, the present invention also provides a method of achieving conception in a mammalian subject utilizing the conception device 10. The method may generally include providing a conception device 10 including a collapsible sidewall 32. As reflected in FIGS. 5A and 5B, the conception device 10 is inserted into the vaginal cavity and positioned over the cervix. The conception device 10 concentrates all available sperm at the opening of the cervical os. As such, the sperm is in contact with the cervical mucous and protected from the environment of the vaginal cavity.

As shown in FIG. 5C, following sexual intercourse, the vaginal cavity relaxes, thereby causing compression of the conception device 10 against and collapsing of the sidewall 32 of the conception device 10. This collapsing of the sidewall 32 brings the closed tip 28 of the device 10 closer to an annular rim 12 of the device while providing a direct path for the sperm supported by the device 10 to the cervical os. The pool of available sperm is placed in an optimum position relative to the cervix. This is of particular significance for a woman having a tilted cervix. If the woman's cervix is tilted (pointed in an abnormal direction), it may not come into contact with the semen pool. A tilted cervix may be the result of anatomy or adhesions that cause it to tilt from something like C-section surgery.

Sperm within the conception device 10 has a much greater opportunity to meet an egg. The sperm do not have to deal with such issues as: making the long journey through the vaginal cavity to the cervix; being pulled out of the vaginal cavity by the penis; becoming lost in the vagina; being flushed from the vagina by gravity; being met by a hostile vaginal environment; or not pooling in the right location to contact the cervix.

With reference now to FIGS. 6-9, another conception device in accordance with the present teachings is illustrated and generally identified at reference character 100. To the extent not otherwise described herein, it will be understood that the device 100 is identical to the device 10 in FIG. 1. In view of the similarities between the embodiments, like reference characters will be used to identify similar features.

The conception device 100 primarily differs from the conception device 10 in that it incorporates one or more ridges 102 for even further directing the predetermined collapse of the conception device 100 by stabilizing the flanges 22 along the annular rim 12, which in turn provide stabilization of the dome 14 over the cervix. It should be understood that the addition of ridges does not impact the strength or the rigidity of the conception device 10, and while it does help provide lateral stability, it does not alleviate problems associated with bunching.

Figure 9:
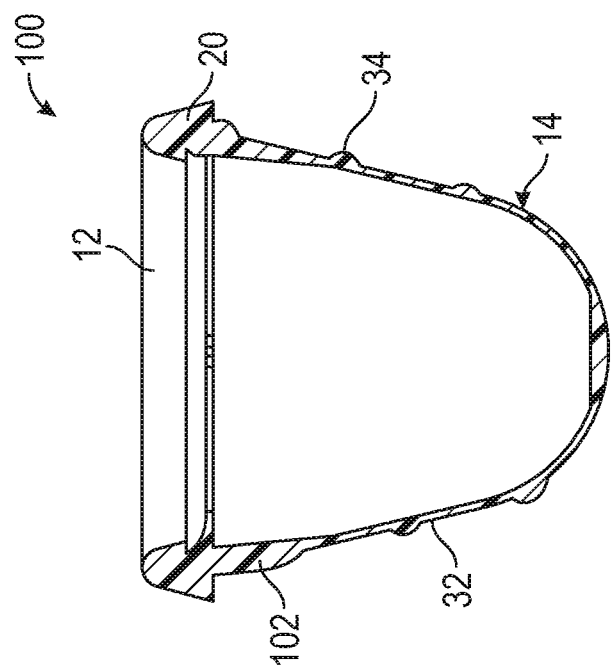
FIG. 9 is a cross-sectional view taken along line 8-8 of FIG. 8.
Figure 8:
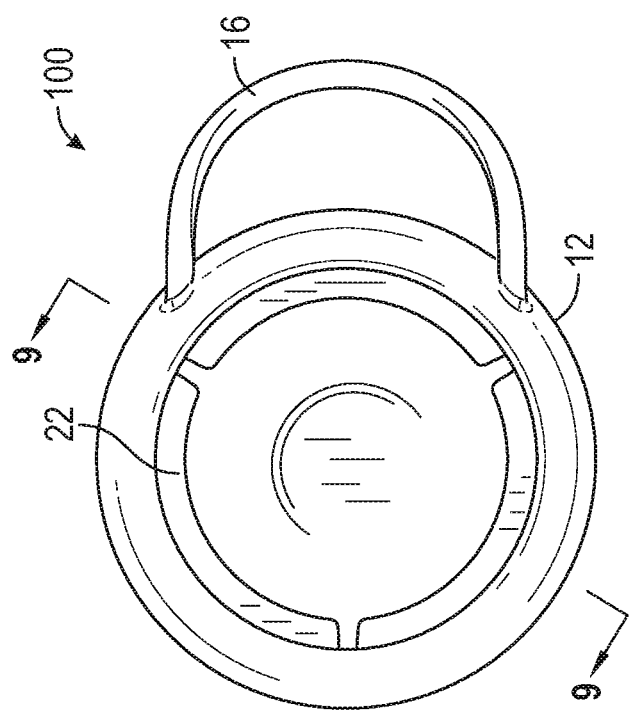
FIG. 8 is a top view of the conception device of FIG. 6.

In the embodiment illustrated, the conception device 100 includes three (3) ribs or ridges 102 formed on the outside of the sidewall 32 and as shown in FIG. 9, connected to the outer surface 20 of the annual rim 12. Further in the embodiment illustrated, the ridges 102 extend downwardly from the annular rim 12 for approximately one-third of the length of the dome 14. The ridges 102 may be positioned equally about the sidewall 32. As perhaps most particularly shown in the cross-sectional view of FIG. 9, the width of the ridges 102 may decrease as the ridges extend downwardly.

It will be appreciated that the device 100 may include a greater or lesser number of ridges 102. Additionally, the ridges need not be positioned equally about the sidewall 32. Furthermore, the particular geometry of the ridges 102 may vary so long as the device 100 collapses in the manner desired while also providing stability of the dome 14 over the cervix.

It will also be appreciated that the device 100 may also include an integral dome rib in the form of spiral ribs 34, ring ribs 36A and 36B, a plurality of discrete raised projections 38C in a spiral ring direction pattern or a plurality of discrete raised projections 38D in a ring-shaped direction pattern. The addition of the integral dome rib effectuates strength, rigidity and lateral stability to the dome 14, and may be used to allow the conception device 10 to be frozen with the sperm inside the receptacle area 26, to allow for a predetermined collapse of the sidewall 32, and to prevent bunching of the conception device 10.

The conception devices 10 and 100 overcome problems that may be associated with a form assuming dome. The general problem with a form assuming dome is that there is little to no control on how the semen is placed on the cervix. In use, the device 10 is placed on the cervix and as the vagina returns to being a potential space the walls of the vagina compress the dome 14. If the dome 14 were form assuming, the semen would move around the exterior of the cervix in an unpredictable manner potentially even taking the majority of the semen and placing it out of contact with the cervical mucus. In an extreme case, the dome of a form assuming device may even form fit at the opening of the cervix and in conjunction with the vaginal wall as well as with the viscosity of the cervical mucus actually block the opening of the cervical os and not permit the semen that has moved around the side of the cervix to be placed in the correct location spot.

The embodiments of conception device 10 described herein provide a dome 14 that is collapsible rather than form assuming. Collapsing of the dome 14 occurs in a predetermined manner due to the thickness of the various portions of the dome 14 and the addition of an integral dome rib in the form of spiral ribs 34, ring ribs 36A and 36B, a plurality of discrete raised projections 38C in a spiral ring direction pattern or a plurality of discrete raised projections 38D in a ring-shaped direction pattern to the dome 14. In all embodiments, the apex of the dome 14 is slightly thicker and the top ⅓ of the dome 14 thinner. As a result, the natural action of the vagina returning to a potential space causes the apex of the dome 14 to come in contact with the opening of the cervical os in a more predictable manner. This predictability may be further enhanced by making the base of the dome 14 slightly more rigid such that the dome 14 will collapse at an intended point which may be approximately ⅔ of the way from the apex. This predictability is also further enhanced by forming, as part of the same unitary construction as the dome 14, an integral dome rib in the form of spiral ribs 34, ring ribs 36A and 36B, a plurality of discrete raised projections 38C in a spiral ring direction pattern or a plurality of discrete raised projections 38D in a ring-shaped direction pattern around the dome 14, and in particular around the base portion 30 and the sidewall 32. In the embodiments illustrated, a first portion of the sidewall 32 adjacent the annular rim may relatively maintain its shape while a second portion of the sidewall 32 proximate the closed tip may collapse.

While specific aspects of a particular embodiment have been described in the specification and illustrated in the drawings, it will be understood by those skilled in the art that various changes may be made and equivalence may be substituted for elements thereof without departing from the scope of the present teachings as defined in the claims. Furthermore, the mixing and matching of features, elements and/or functions may be expressly contemplated herein so that one skilled in the art would appreciate from the present teachings that features, elements and/or functions of one example may be incorporated into other examples as appropriate, unless described otherwise above. Moreover, many modifications may be made to adapt a particular situation or material to the present teachings without departing from the essential scope thereof. Therefore, it may be intended that the present teachings not be limited to the particular examples illustrated by the drawings and described in the specification as the best mode of presently contemplated for carrying out the present teachings but that the scope of the present disclosure will include any embodiments following within the foregoing description and the appended claims.

What is claimed is:

1. A conception device for positioning over a cervix to concentrate semen and promote fertilization, the device comprising:
   an annular rim; and
   a dome formed of a unitary construction extending from the annular rim, the dome defining a receptacle area and including a closed tip, a base portion and a sidewall extending between the closed tip and the base portion, and the dome having an integral dome rib
   wherein the integral dome rib is configured to cause or allow a predetermined collapse of the sidewall in a direction generally perpendicular to the annular rim.

2. The conception device of claim 1, wherein the integral dome rib is a spiral rib extending in a downward spiral around the dome and extending between the base portion to a portion of the sidewall proximate to the closed tip.

3. The conception device of claim 2, wherein the spiral rib is formed of a plurality of discrete raised projections disposed in an end-to-end configuration.

4. The conception device of claim 2, wherein the spiral rib is configured to provide rigidity to cause or allow the predetermined collapse.

5. The conception device of claim 2, further comprising a plurality of ridges outwardly extending from the sidewall, and connecting to the annular rim; and wherein the spiral rib extends on both sides of a ridge of the plurality of ridges.

6. The conception device of claim 5, wherein the sidewall includes a first portion adjacent the annular rim and a second portion proximate the closed tip, the plurality of ridges formed on the first portion.

7. The conception device of claim 2, wherein the spiral rib extends from the annular rim to the portion of the sidewall proximate to the closed tip.

8. The conception device of claim 1, wherein the integral dome rib is one or more ring ribs extending around the dome.

9. The conception device of claim 8, wherein each ring rib of the one or more ring ribs is formed of a plurality of discrete raised projections disposed in an annular or spiral configuration.

10. The conception device of claim 8, wherein there is more than one ring rib and the more than one ring ribs are equidistantly spaced.

11. The conception device of claim 1, wherein the unitary construction has a first thickness at the closed tip, has a second thickness at the sidewall proximate the closed tip, and has a third thickness at the sidewall proximate the annular rim, the second thickness being less than both the first thickness and the third thickness such that the sidewall is collapsible at a portion of the sidewall including the second thickness in a predefined manner due to compression by a vaginal cavity to raise a floor defined by an inner surface of the tip toward the annular rim in the direction generally perpendicular to the annular rim.

12. The conception device of claim 11, wherein the base portion includes a base thickness, the base thickness being greater than the second thickness; and a portion of the sidewall including the second thickness is configured to collapse about a perimeter thereof in the direction perpendicular to the annular rim.

13. The conception device of claim 1, wherein the annular rim and the dome are formed of a material suitable for use in a vagina.

14. The conception device of claim 1, wherein the integral dome rib is configured to restrict bunching up of the device against a side of said cervix.

15. The conception device of claim 1, further comprising two or more flanges extending radially inward from the annular rim about a half millimeter.

16. The conception device of claim 1, wherein the integral dome rib is configured to provide strength, rigidity, and lateral stability to the dome to allow for the device to be frozen with sperm in the receptacle area.

17. The conception device of claim 1, wherein the dome has a length greater than a width.

18. A method of increasing a likelihood of conception in a subject having a cervix, the method comprising the steps of:
(a) providing a conception device having an annular rim, a dome of a unitary construction, the dome including a base portion, a closed tip, a sidewall extending between the closed tip and the annular rim, and the dome having an integral dome rib, wherein the closed tip having a first thickness and the sidewall having a second thickness proximate the closed tip and a third thickness proximate the annular rim, the second thickness being less than both the first thickness and the third thickness, an inner surface of the tip defining a floor;
(b) positioning the annular rim around the cervix to secure the conception device to the cervix; and
(c) collapsing a first portion of the sidewall of the conception device including the second thickness after step (b) in a predefined manner due to compression by a vaginal cavity so as to raise the floor in a direction perpendicular to the annular rim and toward the cervix while providing a direct path to a cervical os for contents within the device and supported by the tip; and
wherein the integral dome rib is configured to cause or allow the collapsing of the first portion.

19. The method of claim 18, wherein the integral dome rib is a spiral rib extending in a downward spiral around the dome and extending between the base portion to a portion of the sidewall proximate to the closed tip.

20. The method of claim 18, wherein the integral dome rib is one or more ring ribs extending around the dome.

21. The method of claim 18, wherein the closed tip and the sidewall are formed of a single material that defines the first and second thicknesses.

22. The method of claim 18, wherein a second portion of the sidewall has a plurality of ridges outwardly extending therefrom, and further comprising maintaining the shape of the second portion of the sidewall with the plurality of ridges.

23. The method of claim 18, further comprising uniformly collapsing a second portion of the sidewall about a perimeter thereof in the direction perpendicular to the annular rim.

24. A conception device for positioning over a cervix to concentrate semen and promote fertilization, the device comprising:
an annular rim; and
a dome of a unitary construction formed of a single material, the dome extending from the annular rim, the dome defining a receptacle area and including a closed tip, a base portion and a sidewall extending between the closed tip and the base portion, and the dome having an integral spiral rib extending in a downward spiral around the dome and extending between the base portion to a portion of the sidewall proximate to the closed tip; and
wherein the integral spiral rib is configured to cause or allow collapse of the sidewall in a predefined manner in a direction generally perpendicular to the annular rim.

25. The conception device of claim 24, wherein the dome has a first thickness at the closed tip, a second thickness at the sidewall proximate the tip and a third thickness at the sidewall proximate the annular rim, the second thickness being less than both the first thickness and the third thickness, such that the sidewall is collapsible at a portion including the second thickness in the predefined manner due to compression by a vaginal cavity to raise a floor defined by an inner surface of the tip toward the annular rim in the direction generally perpendicular to the annular rim.

* * * * *